United States Patent [19]

van den Berg et al.

[11] Patent Number: 5,580,990

[45] Date of Patent: Dec. 3, 1996

[54] PT-CONTAINING COMPOUND, PROCESS FOR ITS PREPARATION, AND APPLICATION OF SUCH COMPOUNDS

[75] Inventors: Franciscus M. van den Berg, Hoofddorp; Edwin L. M. Lempers, Vogelzand; Marieke J. Bloemink, Hofbroeckerlaan; Jan Reedijk, Anthoni Duycklaan, all of Netherlands

[73] Assignees: Stichting Klinische Research Academisch Medisch Centrum, Amsterdam; Rijksuniversiteit Leiden, Leiden, both of Netherlands

[21] Appl. No.: 975,586

[22] PCT Filed: Jul. 16, 1991

[86] PCT No.: PCT/NL91/00126

§ 371 Date: Oct. 29, 1993

§ 102(e) Date: Oct. 29, 1993

[87] PCT Pub. No.: WO92/01699

PCT Pub. Date: Jun. 2, 1992

[30] Foreign Application Priority Data

Jul. 19, 1990 [NL] Netherlands ............................ 9001639

[51] Int. Cl.⁶ ........................ C07D 311/20; C07F 15/00; C12Q 1/70; C12Q 1/68
[52] U.S. Cl. ............................... 549/212; 556/137; 435/5; 435/6; 424/9.36
[58] Field of Search .......................... 435/5, 6; 556/137; 424/9.36

[56] References Cited

U.S. PATENT DOCUMENTS

| | | | |
|---|---|---|---|
| 4,358,535 | 11/1982 | Falkow et al. | 435/5 |
| 4,376,165 | 3/1983 | Hornby et al. | 435/188 |
| 4,490,543 | 12/1984 | Bergquist et al. | 549/212 |
| 4,581,333 | 4/1986 | Kourilsky et al. | 435/6 |
| 4,687,732 | 8/1987 | Ward et al. | 435/6 |
| 4,711,955 | 12/1987 | Ward et al. | 536/29 |
| 5,175,269 | 12/1992 | Stavrianopoulos | 536/27 |
| 5,241,060 | 8/1993 | Engelhardt et al. | 536/27 |
| 5,328,824 | 7/1994 | Ward et al. | 435/6 |

OTHER PUBLICATIONS

Reedijk, J. *Pure Appl. Chem.* 59, 181–192 (1987).
Bauman, J. G. J. et al. *J. Histochem. Cytochem.* 29, 238–246 (1981).
N. P. Johnson, et al., "Structures of the Adducts Formed Between [Pt(dien)Cl]Cl and DNA in vitro", *Nucleic Acids Research*, 10(17): 5255–5271 (1982). Month of publication not provided.
Jean–Pierre Macquet, et al., "A Circular Dichroism Strudy of DNA–Platinum Complexes", *Eur. J. Biochem*, 83: 375–387 (1978). Month of publication not provided.
Jan Reedijk, "The Relevance of Hydrogen Bonding in the Mechanism of Action of Platinum Antitumor Compounds", *Inorganica Chimica Acta*, 198–200: 873–881 (1992). Month of publication not provided.
Sax, N. I. et al. *Hawley's Condensed Chemical Dictionary* (Van Nostrand Reinhold, N.Y.), p. 699 (1987).
Grant, R. et al. *Grant & Hackh's Chemical Dictionary* (McGraw–Hill, N.Y.), p. 337 (1987).
Moeller, T. *Inorganic Chemistry. A Modern Approach* (New York, John Wiley & Sons, 1982), pp. 715–716.
Bauman, J. G. J. et al. "Rapid and High Resolution Detection of in situ Hybridisation to Polytene Chromosome Using Fluorochrome–Labelled RNA". *Chromosoma* (Berl.), vol. 84, pp. 1–18 (1981).

Primary Examiner—Mukund J. Shah
Assistant Examiner—King Lit Wong
Attorney, Agent, or Firm—Hoffmann & Baron

[57] ABSTRACT

Pt-containing compound with the formula $\{Pt^{II}(w)(x)(y)(z)\}$ or $\{Pt^{IV}(u)(v)(w)(x)(y)(z)\}$, wherein u, v, w, x, y and z represent whether or not the same whether or not interconnected ligands, of which at least one is a leaving ligand and at least one of the remaining ligands represents a detectable marker group. According to the invention $(CH_3)_2SO$, Cl or $H_2O$ appears to be suitable as a leaving ligand while as detectable marker group a fluorescent group merits preference and is the ligand fluorescein or tetramethyl rhodamine. A suitable Pt-containing compounds is $\{Pt(ethylenediamine)(Me_2SO)(fluorescein-NH(CS)-NHCH_3)\}$ (PtF). Further, the invention comprises a process for the preparation of the Pt-containing compounds, where the Pt-containing compounds are prepared in a manner known per se for analogous compounds.

16 Claims, No Drawings

PT-CONTAINING COMPOUND, PROCESS FOR ITS PREPARATION, AND APPLICATION OF SUCH COMPOUNDS

Such Pt-containing compounds are known from Reedijk, J. Struct. Bonding (Berlin), 67: 53–72.

This article describes the anti-tumor compound cis-Pt(NH$_3$)$_2$Cl$_2$, which compound has a high affinity for (amongst others) proteins and DNA molecules and particularly it appears that such a compound has a marked affinity for the N7-nitrogen atom in the purine bases Guanine and Adenine, as well as for sulphur groups in macromolecules.

By dissociation of the two chlorine ligands two reactive sites arise, with which such platinum compounds can cross-link between two neighbouring Guanine and/or Adenine bases in the same or in opposite DNA strands. The application of cis-platinum as anti-tumor drug (cytostaticum) is based on this mechanism.

Besides this related carbo-platinum compounds are known from the same literature, which also have a high affinity for amongst others proteins and DNA molecules in a similar way as cis-platinum compounds.

On the contrary monochlorinated platinum compounds like Pt(diene)Cl appear to keep their DNA affinity but they do not form cross-links and interfere only slightly with the base pairing of complementary DNA strands, and are as such not anti-tumor active.

According to U.S. Pat. No. 4,711,955 it is preferred to apply DNA/RNA technology in the present medical-biological practice, especially the diagnostical practice, when non-radioactive nucleic acid labelling techniques are available. The presently applied known non-radioactive labelling techniques for DNA and RNA are globally to be divided in two categories.

1. Labelling which proceeds via enzymatic or organic synthetic routes; for instance biotin, bromodeoxyuridine (BrdU), digoxygenin, fluorescein and peroxidase.
2. Labelling by direct chemical coupling, like photobiotin, AAF, mercury, sulfone groups.

Application of such labels brings along a number of problems, which are particularly related to the complexity of the labelling procedure, the sometimes limited length of the synthetic oligonucleotides which are to be labelled, to use of health-injuring compounds and the stability of the label, when it is bound to the nucleic acid.

The invention now contemplates providing platinum-containing compounds, in the application of which the above-mentioned disadvantages are effectively removed.

To this end the invention provides a compound with the formula $\{Pt^{II}(w)(x)(y)(z)\}$ or $\{Pt^{IV}(u)(v)(w)(x)(y)(z)\}$ with the structural formula 1 or 2 respectively

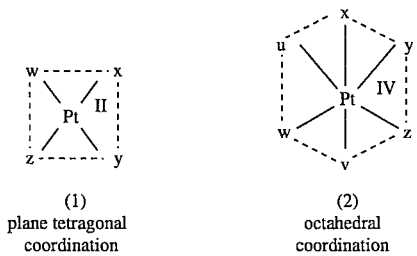

(1) plane tetragonal coordination (2) octahedral coordination in which u, v, w, x, y and z represent whether or not the same whether or not interconnected ligands, from which at least one is a leaving ligand and at least one of the remaining ligands represents a detectable marker group.

Such a compound which is novel per se, and on the one side is provided with a directly or indirectly detectable marker group, as for instance a hapten, fluorescein or rhodamine and on the other side is provided with a suitable leaving group, is an especially suitable and novel DNA label with the general indication PtM (Pt stands for platinum and M stands for marker group) with unique properties.

For it appeared, that such a compound adheres spontaneously and irreversibly to DNA in aqueous medium. Further, the thus labelled DNA may be separated from the redundant compound with the formula 1 or 2 by alcohol precipitation. An important advantage is, that the thus labelled DNA may be detected immediately after hybridization by means of a fluorescence microscope or indirectly with one of the known immunohistochemical staining techniques.

The advantages of the present platinum-containing compounds are shortly summarized:

1. Direct—almost instantaneous—labelling of macromolecules without necessity of enzymatic or organosynthetic procedures.
2. One-step purification of labelled molecules by means of a simple routine technique.
3. Direct and/or indirect detection of labelled molecules by way of almost all known (microscopic) techniques.

As further advantage may be mentioned, that for specific purposes (for instance extra sensitive in situ hybridization of RNA) a radioactive ($^{14}$C or $^{35}$S)-platinum-containing compound according to the invention may be applied as simple and fast (non-enzymatic) labelling of probes, followed by direct detection by means of autoradiography.

Another important new application of the probes labelled with the present compounds is in situ hybridization in the electron microscope whereby the high mass of the platinum atom in the compound according to the invention takes care for a direct probe-specific local increase of the electron density.

As leaving ligand (CH$_3$)$_2$SO, H$_2$O or Cl appears to be especially suitable according to the invention. It is observed that besides the just mentioned preferred leaving ligands in the compound with formula 1 or formula 2, the following groups are qualifying, Br$^-$, I$^-$ or F$^-$; SO$_4^{2-}$, NO$_3^-$, PO$_4^{3-}$, CO$_3^{2-}$, and analogues like ethylnitrate; phosphonates, oxalates, citrates and derivatives thereof; H$_2$O, ROH and RO$^-$, in which R is an organic residual group and substituted sulfoxides R$^1$R$^2$SO, in which R$^1$ and R$^2$ whether or not equal to each other, represent an organic residual group.

As the detectable marker group in the compounds with formula 1 or 2 a fluorescent group generally merits the preference. A special preference merits fluorescein isothiocyanate (FITC) or tetramethyl rhodamine isothiocyanate (TRITC).

A very suitable compound according to the invention is {Pt(ethylenediamine)(Me$_2$SO)(fluorescein-NH(CS)-NHCH$_3$)}, in the following abbreviated as PtF.

The novel compounds according to the invention are especially suitable for virus diagnostic purposes, bacteria diagnostic purposes, for detection of genetic deviations, detection of gene expression, etc.

There are known a number of viruses, which cannot or with great difficulty be brought into culture, and of which the serological diagnostical methods are extremely complicated, or which are very labile outside the body, and therefore unsuitable in contamination tests.

With some of these viruses the diagnosis may moreover be hindered by the necessity of differentiation between an acute stage of the illness, carriership, or virus genome insertion in the human DNA. In the meantime progress has been made herewith by using DNA probes. Some viruses have moreover serious pathogenic effects and are related with the development of malignant tumors. The accurate detection of these viruses and the correlation with a clinical follow-up of patients is therefore an important matter.

In principle virus strains or subtypes may be distinguished from each other by DNA/RNA probes.

Detection methods using labelled DNA or RNA probes appear to be able to solve these problems. Much progress has been made in the diagnosis of both DNA and RNA viruses. The advantage of these methods is that immediately the patient material (smears, samples of blister, nose and other fluids, tissue sections, etc.) may be tested on the presence of virus DNA/RNA. Also retrospective studies have already provided important information about viral causes of mortality etc.

Further, the invention comprises a process for the preparation of Pt-containing compounds according to the invention with the formula $\{Pt^{II}(w)(x)(y)(z)\}$ or $\{Pt^{IV}(u)(v)(w)(x)(y)(z)\}$ with the structural formula 1 or 2,

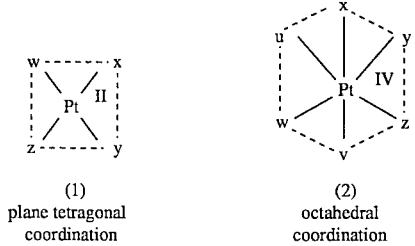

(1) plane tetragonal coordination (2) octahedral coordination in which u, v, w, x, y and z have the aforementioned meanings, characterized in that the Pt-containing compounds are prepared in a manner known per se for analogous compounds.

The preferred compound according to the invention, to wit PtF, is prepared by conversion of fluorescein-N=C=S with $CH_3NH_2$ in water, after which the mentioned fluorescein-NH(CS)NHCH$_3$ is precipitated from the solution by acidifying to a pH of 2–3, after which the precipitate obtained is suspended in water and the pH of the suspension is brought to a value of 10–11 by addition of a base, providing a bright yellow solution, to which solution {Pt(ethylenediamine)(Me$_2$SO)Cl} in water is added and the reaction mixture is stirred at room temperature in the dark, after which the non-reacted fluorescein-NH(CS)NHCH$_3$ is precipitated by acidification and filtered and finally the filtrate is freeze-dried yielding {Pt(ethylenediamine)(Me$_2$SO)(fluorescein-NH(CS)NHCH$_3$)} (PtF).

The preparation of PtF is outlined in the reaction scheme below:

REACTION SCHEME

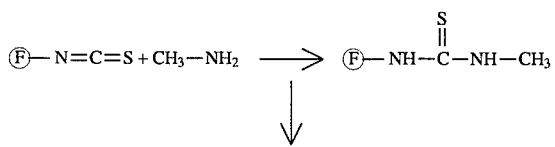

-continued
REACTION SCHEME

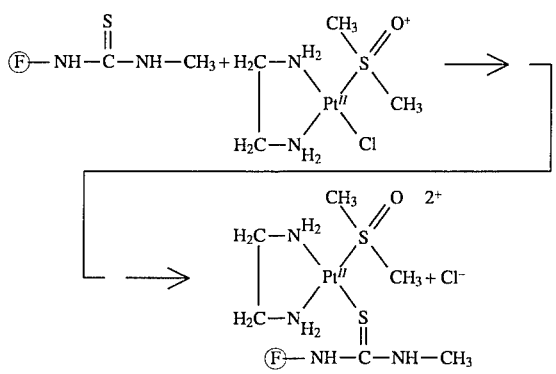

Subsequently, the invention extends to a diagnostic kit for use in the detection of viruses, bacteria, parasites, genetic deviations, gene expression, which kit comprises a Pt-containing compound according to the invention.

The invention is now further elucidated with reference to the following non-limitative examples.

EXAMPLE I

Preparation of PtF for Labelling Purposes

First of all fluorescein-NH(CS)NHCH$_3$ is prepared by reacting 100 mg fluorescein-N=C=S with 1 ml CH$_3$NH$_2$ in 100 ml water. The reaction takes about 1 hour under continuous stirring at room temperature in the dark. The obtained reaction product, fluorescein-NH(CS)NHCH$_3$, is precipitated from the solution by acidifying with HCl (1 mol/liter {M}) to a pH of 2–3. The precipitate is washed in water and then collected.

Then a suspension of 100 mg (0.237 mmol) of the thus obtained fluorescein-NH(CS)NHCH$_3$ in 95 ml of water was brought with NaOH (1M) on a pH of 10–11, whereby a bright yellow solution was obtained. To this solution was added 72 mg (0.178 mmol) of [Pt(ethylenediamine)(Me$_2$SO)Cl]Cl or [Pt(ethylenediamine)Cl$_2$]Cl in 5 ml of water and the reaction mixture was slowly stirred in the dark for 5–10 minutes at room temperature. The non-reacted fluorescein-NH(CS)NHCH$_3$ was precipitated by acidification to a pH of 2–3 with HCl (1M) and removed by filtration. The bright yellow filtrate was freeze-dried, yielding a stable dry compound {Pt(ethylenediamine)(Me$_2$SO)(fluorescein-NH(CS)NHCH$_3$)}, or {Pt(ethylenediamine)Cl(fluorescein-NH(CS)NHCH$_3$)}, abbreviated PtF.

In principle the reaction may be carried out in an analogous manner with as starting material the one as mentioned above, provided that fluorescein is replaced by for instance rhodamine, 7-amino-4-methylcoumarin-3-acetic acid, biotin, digoxygenin or any other hapten, which may be modified in such a manner that therein is present a double-bonded sulphur (S) atom, a —SR group, a NR'R" group or a nitrogen ring (—N—), wherein R'R" are equal or not equal to each other and represent an organic residual group. (Also H is possible). These S- or N-atoms serve as binding ligand for the platinum (Pt) atom.

EXAMPLE II

Nucleic Acid-Labelling With PtF

The dry PtF compound is dissolved at a concentration of 1 mg/ml in distilled water, which has been brought at a pH of 9–10 with NaOH.

Then DNA (single or double stranded) or RNA at an arbitrary concentration (for instance 100 µg/ml) was taken up in a low-salt buffer with a pH of about 8 (for instance 10 mM TRIS-HCl) and possibly fragmented by ultrasonication.

To the thus obtained nucleic acid solution a ten fold molar excess of PtF solution was added and after proper mixing the reaction mixture was incubated in the dark at room temperature for 30–60 minutes.

Next 1/10 volume part of a Na acetate (3M) solution of a pH of 5.6 was added to the reaction mixture and after mixing subsequently two parts of ethanol were added, after which it was thoroughly stirred and the reaction vial was then incubated for 15 minutes at 80° C. or for 2 hours at –20° C.

The PtF-labelled nucleic acid was thereupon precipitated by centrifugation at 10.000×g for 7 minutes. The obtained pellet was washed in 90% ethanol and the nucleic acid labelled with the PtF was dissolved at the desired concentration at an arbitrary buffer (for instance 10mM TRIS-HCl a pH of 7.5, 0.3 mM EDTA).

The thus PtF-labelled nucleic acid is now ready for use.

Examples of the Use of PtM-Labelled Nucleic Acids

EXAMPLE III

Human papilloma virus cannot be cultured, but some subtypes (HPV 16/18) are positively connected with the origin of malignant tumors of amongst others the cervix and the penis.

By now labelling purified DNA of such a papilloma virus with PtM and then performing an in situ hybridization procedure on cells or tissue of for instance the cervix, the presence of the risk bearing type papilloma virus may be shown very specifically by means of a direct fluorescence procedure or an indirect immunohistochemical procedure with anti-PtM antibodies.

EXAMPLE IV a) Human papilloma virus cannot be cultured, but some subtypes (HPV 16/18) are positively connected with a large chance on the development of malignant tumors on cervix or penis. Further, probes are developed for amongst others the detection of DNA (Vaccinia, Herpes simplex (HSV½, Epstein Barr, and adenovirus)) and RNA viruses (Rota virus, influenza A, Cocksackie B). Until present the diagnosis of acute infection with Hepatitis B virus is only possible by inoculation of chimpanzees (!), for the virus cannot be cultured in human cells.

b) Varicella zoster virus, too, is very difficult to culture: it lasts 5–14 days, before a culture may be assessed. Moreover the virus is very labile and may become inactivated during transport. A negative test is therefore no proof of absence of the illness. Over and above a VZV infection is on morphological grounds indistinguishable from infections with Herpes simplex virus. Even commercially available antisera do not give an answer in immunohistochemical tests.

c) Cytomegalo virus is very laboriously cultured; diagnoses within a week's time are impossible, within 6 weeks no exception. CMV infections form an important source of complications in transplant-patients and in patients with reduced defence (AIDS). A good monitoring of these patients is essential.

In the above-mentioned cases a, b and c, which figure as only some of the many possibilities of examples of virus diagnostics, diagnostics may be considerably simplified and accelerated by the application of hybridization techniques with PtM-labelled probes.

EXAMPLE V

Bacteria Diagnostics

It appeared to be possible recently to detect also bacterial nucleic acids using DNA probes. Genes for bacterial toxins may be shown; however, it is not possible to discern whether these genes are expressed. Fast detection of chromosomal and plasmid coded virulence factors (amongst others *Listeria monocytogenes, Clostridium perfringens* enterotoxin, *Vibrio cholerae* enterotoxin, *E. coli* enterotoxins and invasivity, *Shigella* and *Yersinia enterocolitica* enteroinvasivity) are important applications in the diagnosis of food poisoning and the quality control in the food industry (end product control).

Detection of *Helicobacter* (formerly *Campylobacter*) *pylori* by DNA in situ hybridization with PtM probes in stomach biopsies of patients with gastritis is possible.

Also the DNA of *Chlamydia trachomatis* may be detected in for instance a sandwich assay, or by means of an in situ hybridization.

EXAMPLE VI

Diagnostics of Parasitic Infections

World-wide 2 millions of people pass away of malaria. In principle this can be prevented by timely correct diagnostics. The present (routine) microscopic methods are often all too complicated for third world countries. In the western world the difficult microscopic technique may be extended with in situ hybridization on routine preparations, using PtM probes. Through this differential diagnostics of malaria species is considerably simplified and can be carried out by minimally trained personnel. In the third world a dipstick test based on PtM is the appropriate route for fast and simple diagnostics.

As analogous examples may be valid infection illnesses caused by *Schistosoma, Trypanosoma, toxoplasmas*, etc.

EXAMPLE VII

Detection of Genetic Deviations

The hybridization technique with PtM probes offers the possibility for prenatal diagnostics of congenital deviations in for instance amniotic fluid punctates and chorionbioses. Postnatal detection of deviations (for instance malignities) is also possible, as well as extension of HLA typification for diagnosis of HLA associated illnesses.

Restriction fragment polymorphisms: Every human genome will fall apart, when treated with restriction enzymes, in a large number of specific fragments: the restriction fragments. If by a mutation the base sequence changes on a site where a restriction enzyme attacks, will this lead to the development of aberrant fragments. These fragments may be detected by suitable (PtM labelled) probes by means of DNA blotting methods (for instance in sickle cell anaemia, Duchenne muscular dystrophy, cystic fibrosis, Huntington chorea).

Immediate detection of aberrant DNA with synthetic oligonucleotide probes may take place when the base sequence belonging to a DNA deviation is known (β-thalassemia, anti-thrombin III deficiency, growth hormones deficiency, haemophilia B, PKU . . . etc.).

Detection of chromosome changes as translocations, deletions, inversions and duplications in the human karyotype may be detected by means of in situ hybridization followed by direct PtF fluorescence, or by Southern blotting of restriction fragments.

EXAMPLE VIII

Detection of Gene Expression

The visualization of the presence of a cellular antigen using immunochemical techniques does not prove that at that moment the relative gene are expressed. Neither does this indicate whether the shown product has an intra- or extracellular origin. Detection of mRNA within a cell gives direct information about the expression of genes. This information may provide data on cell functioning, but may also be of assistance in diagnostics.

In view of the present problems for carrying out this RNA ISH (RISH) technique with non-radioactive probes, the application of the very direct PtM label is the appropriate way of performing such diagnostics because the problems particularly arise from the necessity to dispose of a well-penetrating immunohistochemical detection system. This last one may remain in abeyance with the application of direct PtM fluorescence.

Detection of deviating mRNA as a mark of heritable illnesses by means of blotting with radioactive cDNA probes has been proven to be possible already for a number of congenital deviations. The speed and applicability may be considerably increased here by non-radioactive (or radioactive) PtM labelling.

With PtM probes RISH or blotting may be applied in the diagnosis of cancer by means of detection of specific gene transcripts (for instance calcitonin mRNA in thyroid gland metastases, oncogene expression in malignant tumors), or the loss of germ line bands (loss of heterozygosity) or gene rearrangement (lymphomas).

We claim:

1. Pt-containing compound for use in detectably labeling a nucleic acid molecule, with the formula $\{Pt^{II}(w)(x)(y)(z)\}$ or $\{Pt^{IV}(u)(v)(w)(x)(y)(z)\}$, with the structural formula 1 or 2:

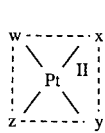 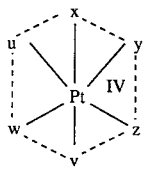

(1)      (2)

in which u, v, w, x, y, and z represent whether or not the same whether or not covalently interconnected ligands, of which no more than one of the ligands is a leaving ligand selected from the group consisting of halide, sulfate, nitrate, phosphate, carbonate, ethylnitrate, phosphonates, oxalates, citrates, $H_2O$ ROH, $RO^-$, in which R is an organic residual group; and substituted sulfoxides $R^1R^2SO$, in which $R^1$ and $R^2$ whether or not equal to each other are organic residual groups, at least one of the ligands is a detectable marker group, and the remaining ligands are one or more ethylenediamine moieties.

2. Compound according to claim 1, wherein the leaving ligand is $(CH_3)_2SO$, Cl, or $H_2O$.

3. Compound according to claim 1, wherein the detectable marker group is a fluorescent group.

4. Compound according to claim 3, wherein the fluorescent group is fluorescein or tetramethyl rhodamine, or either compound optionally modified to include a Pt-binding linkage structure containing a double-bonded S atom, a —SR group, a $NR^3R^4$ group or a nitrogen-containing ring, wherein R is an organic residual group and $R^3$ and $R^4$ are independently hydrogen atoms or organic residual groups.

5. The Pt-containing compound according to claim 1, wherein the detectable marker group is fluorescein, rhodamine, 7-amino-4-methylcoumarin-3-acetic acid, biotin or other hapten, digoxygenin, a radioactive moiety, or an immunohistochemically detectable moiety, and wherein said detectable marker group is optionally modified to include a Pt-binding linkage structure containing a double-bonded S atom, a —SR group, a $NR^3R^4$ group or a nitrogen-containing ring, wherein R is an organic residual group and $R^3$ and $R^4$ are independently hydrogen atoms or organic residual groups.

6. The Pt-containing compound according to claim 1, wherein the detectable marker group is biotin optionally modified to include a Pt-binding linkage structure containing a double-bonded S atom, a —SR group, a $NR^3R^4$ group or a nitrogen-containing ring, wherein R is an organic residual group and $R^3$ and $R^4$ are independently hydrogen atoms or organic residual groups.

7. The Pt-containing compound according to claim 1, having the structure:

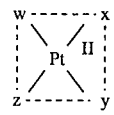

wherein w is said leaving groups, x is biotin optionally modified to include a Pt-binding linkage structure containing a double-bonded S atom, a —SR group, a $NR^3R^4$ group or a nitrogen-containing ring, wherein R is an organic residual group and $R^3$ and $R^4$ are independently hydrogen atoms or organic residual groups, and y and z together are ethylenediamine.

8. $\{Pt(ethylenediamine)Cl(fluorescein-NH(CS)NHCH_3)\}$.

9. $\{Pt(ethylenediamine)(Me_2SO)(fluorescein-NH(CS)-NHCH_3)\}$.

10. A process for preparing the compound of claim 9, comprising:

(a) reacting fluorescein-N=C=S with $CH_3NH_2$ in water to produce fluorescein-NH(CS)NHCH$_3$;

(b) acidifying said fluorescein-NH(CS)NHCH$_3$ to a pH of about 2–3 to precipitate said fluorescein-NH(CS)NHCH$_3$;

(c) resuspending said precipitate in water;

(d) adjusting the pH of the suspension of fluorescein-NH(CS)NHCH$_3$ to about 10–11 to obtain a bright yellow solution;

(e) reacting the basified fluorescein-NH(CS)NHCH$_3$ with Pt(ethylenediamine)(Me$_2$SO)Cl in water while stirring at room temperature in the dark;

(f) precipitating the non-reacted fluorescein-NH(CS)NHCH$_3$ by adjusting the pH of the reaction mixture to about 2–3; and (g) filtering and freeze-drying the supernatant from step (f), yielding Pt(ethylenediamine)(Me$_2$SO)(fluorescein-NH(CS)-NHCH$_3$).

11. A method for the diagnosis of viral, bacterial, or parasitic infections, detection of genetic deviation, or detection of gene expression, comprising detecting a detectably labeled nucleic acid specific for a viral, bacterial, or parasitic infection, genetic deviation, or gene expression, wherein said detectably labeled nucleic acid is labeled with a Pt-containing compound with the formula {Pt$^{II}$(w)(x)(y)(z)} or {Pt$^{IV}$(u)(v)(w)(x)(y)(z)}, with the structural formula 1 or 2:

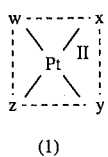
(1)

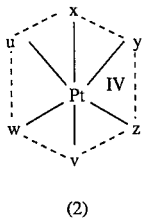
(2)

in which u, v, w, x, y and z represent whether or not the same whether or not covalently interconnected ligands, of which no more than one of the ligands is said nucleic acid molecule, at least one of the ligands is a detectable marker group, and the remaining ligands are one or more ethylenediamine moieties.

12. The method according to claim 11, wherein the detectable marker group is a fluorescent group.

13. The method according to claim 12, wherein the fluorescent group is fluorescein or tetramethyl rhodamine or either compound optionally modified to include a Pt-binding linkage structure containing a double-bonded S atom, a —SR group, a NR$^3$R$^4$ group or a nitrogen-containing ring, wherein R is an organic residual group and R$^3$ and R$^4$ are independently hydrogen atoms or organic residual groups.

14. The method according to claim 11, wherein the detectable marker group is fluorescein, rhodamine, 7-amino-3-methylcoumarin-3-acetic acid, biotin or other hapten, digoxygenin, a radioactive moiety, or an immunohistochemically detectable moiety, and wherein said detectable marker group is optionally modified to include a Pt-binding linkage structure containing a double-bonded S atom, a —SR group, a NR$^3$R$^4$ group or a nitrogen-containing ring, wherein R is an organic residual group and R$^3$ and R$^4$ are independently hydrogen atoms or organic residual groups.

15. The method according to claim 11, wherein the detectable marker group is biotin optionally modified to include a Pt-binding linkage structure containing a double-bonded S atom, a —SR group, a NR$^3$R$^4$ group or a nitrogen-containing ring, wherein R is an organic residual group and R$^3$ and R$^4$ are independently hydrogen atoms or organic residual groups.

16. The method according to claim 11, wherein said Pt-containing compound has the structure:

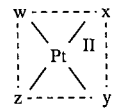

wherein w is said nucleic acid molecule, x is biotin optionally modified to include a Pt-binding linkage structure containing a double-bonded S atom, a —SR group, a NR$^3$R$^4$ group or a nitrogen-containing ring, wherein R is an organic residual group and R$^3$ and R$^4$ are independently hydrogen atoms or organic residual groups, and y and z together are ethylenediamine.

* * * * *